US006997947B2

(12) United States Patent  
Walak et al.

(10) Patent No.: US 6,997,947 B2  
(45) Date of Patent: Feb. 14, 2006

(54) MULTI-PROPERTY NITINOL BY HEAT TREATMENT

(75) Inventors: Steven E. Walak, Natick, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 289 days.

(21) Appl. No.: 10/304,249

(22) Filed: Nov. 26, 2002

(65) Prior Publication Data

US 2003/0109918 A1    Jun. 12, 2003

Related U.S. Application Data

(62) Division of application No. 09/362,261, filed on Jul. 28, 1999, now Pat. No. 6,485,507.

(51) Int. Cl.  
*A61F 2/06*      (2006.01)

(52) U.S. Cl. .................................... 623/1.18

(58) Field of Classification Search ......... 623/1.18–1.2  
See application file for complete search history.

(56) References Cited

U.S. PATENT DOCUMENTS

| | | | |
|---|---|---|---|
| 3,012,882 A | | 12/1961 | Muldawer et al. |
| 3,174,851 A | | 3/1965 | Buehler et al. |
| 5,069,226 A | | 12/1991 | Yamauchi et al. |
| 5,104,404 A | | 4/1992 | Wolff |
| 5,171,383 A | * | 12/1992 | Sagae et al. ................ 148/564 |
| 5,197,978 A | | 3/1993 | Hess |
| 5,383,892 A | * | 1/1995 | Cardon et al. ............. 623/1.16 |
| 5,540,712 A | | 7/1996 | Kleshinski et al. |
| 5,597,378 A | | 1/1997 | Jervis |

(Continued)

FOREIGN PATENT DOCUMENTS

EP     0 796 597 A2     9/1997

(Continued)

*Primary Examiner*—Eduardo C. Robert  
*Assistant Examiner*—Annette Reimers  
(74) *Attorney, Agent, or Firm*—Vidad, Arrett & Steinkraus

(57) ABSTRACT

Medical devices may be made of shape-memory materials portions of which have been heat treated to exhibit spatial variations in the stiffness of the material. Devices including stents, vena cava filters and guidewires may be constructed from such materials. Devices may also be made from shape-memory materials which have been locally heat treated such that the superelasticity of the treated portion is destroyed while the remainder of the shape-memory material can transition between the martensitic and austenitic states.

22 Claims, 8 Drawing Sheets

U.S. PATENT DOCUMENTS

| | | |
|---|---|---|
| 5,709,704 A | 1/1998 | Nott et al. |
| 5,769,796 A | 6/1998 | Palermo et al. |
| 5,776,100 A * | 7/1998 | Forman ................. 604/102.03 |
| 5,836,893 A | 11/1998 | Urick |
| 5,836,969 A | 11/1998 | Kim et al. |
| 5,843,244 A | 12/1998 | Pelton et al. |
| 5,846,247 A | 12/1998 | Unsworth et al. |
| 5,853,419 A * | 12/1998 | Imran ......................... 623/1.15 |
| 5,868,783 A * | 2/1999 | Tower ........................ 623/1.16 |
| 5,902,317 A | 5/1999 | Kleshinski et al. |
| 5,938,697 A * | 8/1999 | Killion et al. .............. 623/1.15 |
| 6,146,417 A | 11/2000 | Ischinger |
| 6,425,855 B1 * | 7/2002 | Tomonto ..................... 600/36 |
| 6,485,507 B1 | 11/2002 | Walak et al. |
| 6,585,753 B1 * | 7/2003 | Eder et al. ................. 623/1.15 |

FOREIGN PATENT DOCUMENTS

| | | |
|---|---|---|
| EP | 0 830 853 A1 | 3/1998 |
| WO | 95/31945 | 11/1995 |
| WO | 97/38747 | 10/1997 |
| WO | 98/07386 | 2/1998 |
| WO | 98/39049 | 9/1998 |

\* cited by examiner

MULTI-PROPERTY NITINOL BY HEAT TREATMENT

This application is a Divisional of U.S. application Ser. No. 09/362,261, filed Jul. 28, 1999 and issued as U.S. Pat No. 6,485,507 the contents of which is incorporated herein in its entirety by reference.

BACKGROUND OF THE INVENTION

The present invention is related to the use of shape memory materials in medical devices.

A shape memory material can assume an initial high temperature configuration and a deformed low temperature configuration and revert back to the initial high temperature configuration upon the application of heat. The high temperature configuration of the material is set into the material or memorized during an initial shaping step in which the material is maintained at a high temperature in a desired shape for a period of time.

This shape memory exhibited by metals results from the metal undergoing a reversible solid state phase transition. Specifically, the metal transitions from an austenitic state to a martensitic state with a decrease in temperature. The temperature at which the transition begins is typically designated $M_s$ (martensite start temperature) while the temperature at which the transition finishes is designated $M_f$ (martensite finish temperature). As the metal transitions from the austenitic state to the martensitic state it becomes more easily deformed. In the martensitic state, the metal is able to accommodate significant plastic deformation at an almost constant stress level.

Upon heating a metal in the martensitic state, the metal begins to return to an austenitic state. The temperature at which this transition begins to occurs is designated $A_s$ (Austenitic start temperature). The transition is complete at a temperature designated $A_f$ (Austenitic finish temperature). When $A_f$ is attained, the metal has fully reverted to its initial, high temperature configuration.

Shape-memory materials have been disclosed in U.S. Pat. No. 3,012,882 to Muldawer et al. and U.S. Pat. No. 3,174,851 to Buehler et al. both of which are incorporated herein by reference in their entirety.

A variety of materials exhibit shape memory properties including binary metals such as Nickel-Titanium alloys including Nitinol. Doped Nickel-Titanium alloys may also exhibit shape-memory properties.

The use of shape-memory metals in medical applications has been disclosed in a number of references including U.S. Pat. No. 5,197,978 to Hess, U.S. Pat. No. 5,540,712 to Kleshinski et al., U.S. Pat. No. 5,597,378 to Jervis, U.S. Pat. No. 5,769,796 to Palermo et al., U.S. Pat. No. 5,846,247 to Unsworth et al. The contents of the above patents are incorporated herein in their entirety by reference.

Shape-memory materials have been used, inter alia, in the production of stents. Nitinol stents which are fully expanded in the austenitic state and compressed or partially expanded in the martensitic state have been disclosed. The specific Nitinol alloy is chosen such that the stent will be in the austenitic state at body temperature. Prior to insertion into the body, the stent is maintained at low temperature corresponding to a temperature within the martensitic range. Upon delivery to a desired bodily location, the stent is warmed to at least the $A_f$ temperature and in the process expanded to its desired final diameter.

Shape-memory metals have been disclosed for use in other medical devices as well.

The physical properties, including elasticity and stiffness, of a shape-memory metal may be controlled via a variety of factors including the chemical composition of the alloy and the treatment to which the alloy is subjected. Commonly assigned U.S. patent application Ser. No. 09/008,684, incorporated herein in its entirety by reference, discloses a process for improving the ductility of Nitinol via control of a number of process parameters. The physical properties of a shape-memory material may also be controlled by heat treating the material. By selective local heat treatment of a shape-memory material, it is possible to destroy the austenitic-martensitic transition and/or change the elasticity and stiffness.

BRIEF SUMMARY OF THE INVENTION

The present invention is directed to medical devices which use shape-memory materials that have been differentially heat treated to exhibit spatially varying properties such as elasticity and stiffness.

The present invention is directed to medical devices having been formed, at least in part, from shape-memory materials which have been locally treated to alter their memory characteristics relative to portions of the device which have not been subjected to the local heat treatment. Specifically, a region of the shape-memory material is treated to decrease the stiffness of the region relative to the remainder of the medical device. Desirably, the local treatment will destroy the superelastic properties of the locally treated region.

The invention is directed in particular to a stent having been formed at least in part of a shape-memory material. The stent comprises a plurality of cells arranged in columns extending from one end of the stent to the other. Adjacent columns of cells are interconnected. The stent includes at least one differently treated column of cells which has been treated differently from the remainder of the stent to have different shape-memory properties from the remainder of the stent.

The invention is also directed to a stent wherein at least one of the columns is characterized by a reduced elasticity relative to the remainder of the columns.

The invention is also directed to a stent wherein at least one of the columns is characterized by a reduced stiffness relative to the remainder of the columns.

The invention is further directed to a stent wherein at a desired temperature range, at least one longitudinal column of cells does not have superelastic properties while the remainder of the longitudinal columns do have superelastic properties.

The invention is also directed to a stent having been formed of a shape memory material and comprising a plurality of spaced segments. Adjacent spaced segments are connected to each other by one or more connector sections. Each segment comprises a series of interconnected cells. Desirably, the cells in plan view are of polygonal configuration. The segments have been subjected to a different heat treatment than the connector sections.

The invention is also directed to a stent having been formed of a shape memory material and comprising a plurality of spaced segments with adjacent spaced segments connected to each other by one or more connector sections. Each segment comprises a series of interconnected cells. Desirably, the cells in plan view are of polygonal configuration. The segments have a reduced stiffness relative to the connector sections. Desirably, the segments are not superelastic.

In another embodiment, the invention is directed to a medical guidewire having been formed at least in part of a shape-memory metal. Different portions of the shape-memory metal have been treated differently to have different shape-memory properties. Desirably, at least one portion of the guidewire is subjected to a local heat treatment resulting in a reduced stiffness compared with the remainder of the guidewire. In this way, a guidewire of desired flexibility can be prepared. Via the localized heat treatment, a guidewire may be prepared in which at least a portion thereof retains its shape memory properties while a portion thereof loses its shape memory properties.

In yet another embodiment, the invention is directed to implantable medical filters such as vena cava filter having been formed of shape-memory materials. At least a portion of the shape-memory material is differently treated to alter the shape-memory properties of the material relative to the untreated shape-memory material. Desirably, the differently treated portion will be heat treated and exhibit a greater tendency toward plastic deformation relative to the remainder of the filter.

BRIEF DESCRIPTION OF THE SEVERAL VIEWS OF THE DRAWING(S)

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

The present invention is directed to the selective treatment of portions of a medical device containing a shape memory material. More specifically, the invention is directed to differential treatment of the shape memory material in a medical device to achieve different physical properties in different portions of the device.

Medical devices made of a shape memory material such as Nitinol typically have shape memory characteristics. The shape memory characteristics of the material may be altered by heat treating the material. By locally treating portions of a shape-memory metal, it is possible to produce a metal with spatial variations in the elasticity and stiffness of the metal. The locally treated portions will initiate plastic deformation at a lower strain than the portions that have not been locally treated. Depending on the extent of the heat treatment, the material may simply have a reduced stiffness in the locally treated portion or the superelasticity of the locally treated portion may be destroyed with the locally treated portion being plastically deformable.

Figure 1:
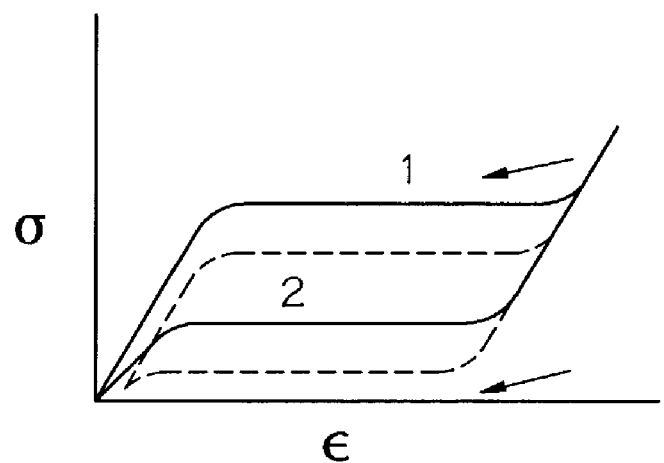
FIG. 1 illustrates the stress-strain behavior of an alloy which can undergo a transition from a martensitic state to an austenitic state and the stress-strain behavior of the alloy following additional heat treatment.

In FIG. 1, a stress-strain curve (solid line) is shown for a shape-memory material. The stress-strain curve (dashed line) for the same material following additional heat treatment of the material is also shown. As a result of the heat treatment, the material has a reduced load and unload plateau, as shown in FIG. 1 and the material initiates plastic deformation at a lower strain level.

Figure 2:
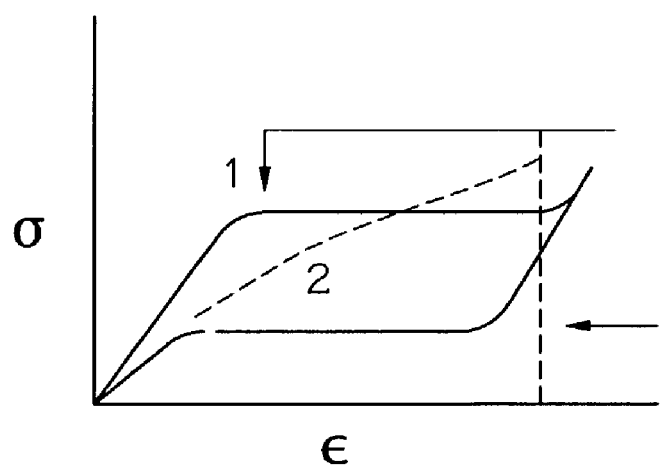
FIG. 2 illustrates the stress-strain behavior of an alloy which can undergo a transition from a martensitic state to an austenitic state and the stress-strain behavior of the alloy following additional heat treatment.

It has also been found that with sufficient heat treatment, the superelastic properties of the material may be destroyed. In FIG. 2, the stress-strain curve (solid line) is shown for a shape-memory material. The stress-strain curve (dashed line) for the same material following significant additional heat treatment to eliminate the superelastic properties of the material is also shown in FIG. 2.

The shape memory material based medical device is typically subject to a first annealing using standard annealing processing conditions as are known in the art. Desirably, the device will be annealed for about 5 minutes to about 40 minutes at a temperature ranging from about 400 C. to about 575 C. More desirably, the device will be annealed for about 10 minutes to about 15 minutes. Also more desirably, the device will be annealed at a temperature ranging from about 450 C. to about 550 C. Shorter or longer periods may be used as may higher or lower temperatures, depending on the material being annealed and the desired properties of the material.

Following the first annealing, the medical device is subjected to a second, localized, annealing step in which the device is heated further. The localized heat treatment of the desired shape-memory material medical device may be accomplished by any suitable method. One such suitable method involves the use of electrical resistance heating. Electrical leads are attached across the desired portion of the device and a current allowed to pass therethrough. Because of the resistance of the shape-memory metal, the desired portion of metal heats up thereby further annealing the material. The technique has been applied to a stent made of Nitinol wire (0.014 inch diameter). Leads were attached to a desired portion of the stent and 4 Volts applied to the wire. After 20 seconds, the desired portion of the wire transitioned from a superelastic state to a plastic state.

Another suitable method involves applying a heated inert gas jet to a desired portion of the medical device to selectively heat a desired portion of the device. Yet another method involves the use of an induction coil. An induction coil may be placed over a desired portion of the medical device to effect induction heating of the desired portion of the medical device. A laser may also be used to selectively heat desired regions of the medical device. The desired regions of the medical device may also be brazed. The medical device may also be placed in a heat treating fluid such as a salt bath or a fluidized sand bath with appropriate sections of the device insulated.

Regardless of the method chosen for the second annealing step, the second annealing step is typically carried out at a temperature of about 550 C. to about 600 C. for about five minutes to about 20 minutes. At such temperatures, the stiffness of the material will be reduced. As with the first annealing step, the exact time and temperature of the second annealing step depends on the material chosen (i.e. its composition) and on the form of the material (for example, in wire form or in sheet form). In certain cases, it may be desirable for the second annealing step to be carried out over shorter or longer periods of time and at lower or higher temperatures than those disclosed above. In one embodiment of the invention, it is desirable to locally heat treat the material during the second annealing step to destroy the shape memory feature of the metal in the treated region by treating the desired portions of the stent at temperatures of about 650 C. to about 700 C. and above. At temperatures of about 600 C. to about 650 C., whether the heat treatment destroys the shape memory feature depends on the duration of the treatment and the composition of the material.

The invention contemplates localized heat treating of a variety of medical devices including stents, medical guidewires and filters such as vena cava filters. For the purposes of this disclosure, it is understood that the term 'stent' is intended to include a variety of related devices including stents, grafts and stent-grafts in particular and endoluminal prostheses in general.

Figure 3A:
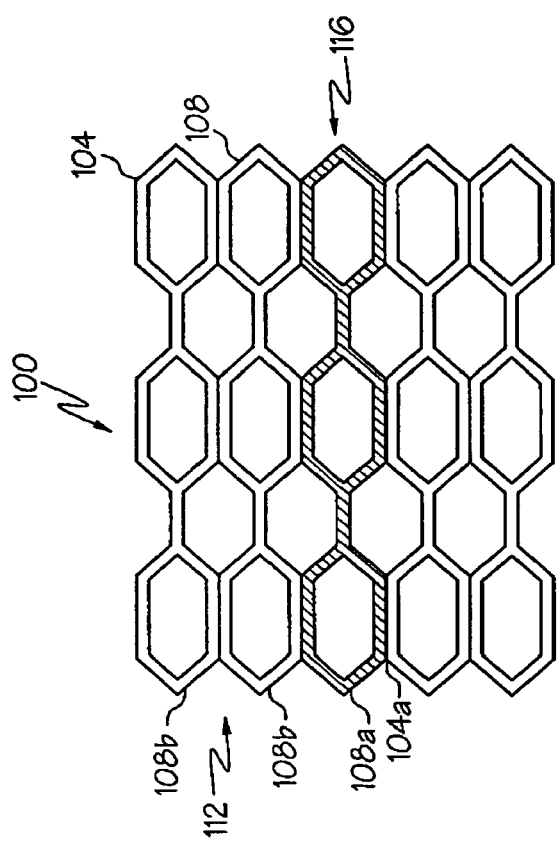
FIG. 3a is a side-elevational view of a stent made in accordance with the present invention.

In one embodiment, as shown in FIG. 3a, the invention is directed to a stent, shown generally at 100, comprised of a plurality of cells 104 arranged in columns 108 extending from one end 112 of the stent to the other end 116. Adjacent columns 108 of cells 104 are interconnected. The stent includes at least one differently treated column 108a of cells 104a which has been treated differently from the remainder of columns 108b to have different shape-memory properties from the remainder of the stent.

Desirably, differently treated column 108a will be characterized by an increased tendency to plastic deformation relative to the remainder of the stent and will be plastically deformable. More desirably, the superelasticity of the differently treated portion will be destroyed as a result of the heat treatment.

The invention also contemplates treating the column(s) such that the treated portion loses its shape memory characteristic.

Figure 3B:
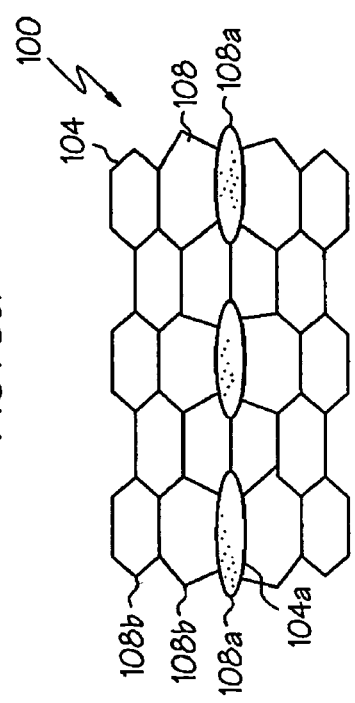
FIG. 3b is a side-elevational view of the stent of FIG. 3 in which the treated column of cells has not been fully expanded.

FIG. 3b shows the stent of FIG. 3a in a partially expanded state. Untreated columns 108b are shown in an expanded state, having been exposed to a sufficient temperature to cause the metal to transition to its austenitic state. Treated column 108a is in an unexpanded state, the superelastic properties of the material having been locally destroyed.

Although columns 108b are fully expanded, stent 100 may be further expanded by applying a radially outward force to the stent thereby opening or expanding treated column(s) 108a. A balloon catheter or other expansion device may be used to effect such a 'touch-up' expansion of the stent.

By providing a column of cells of different shape memory properties which are not expanded in concert with the expansion of the remainder of the stent, the stent may later be 'touched up' via mechanical expansion of the cells of the treated column to better fit in a lumen.

Figure 4A:
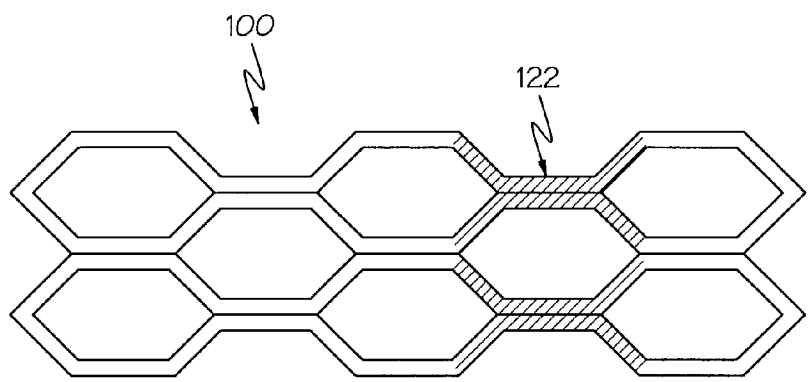
FIG. 4a is a side elevational view of a stent made in accordance with the present invention.
Figure 4B:
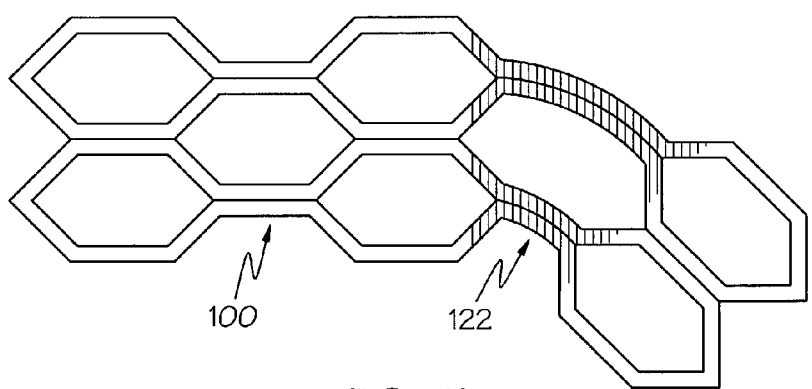
FIG. 4b is a side elevational view of the stent of FIG. 4a after it has been bent.

Another stent formed in accordance with the present invention is shown generally at 100 in FIGS. 4a and 4b. One or more circumferential bands of cells 122 is specially treated, in accordance with the invention. Bands 122 have different shape memory properties from the cells in the remainder of the stent. For example, band(s) 122 may be plastically deformable. FIG. 4a depicts stent 100 prior to being deformed at band 122 while FIG. 4b depicts stent 100 after it has been bent at band 122. The remainder of the stent which has not been subjected to the special treatment retains the shape memory properties of the material.

Figure 5A:
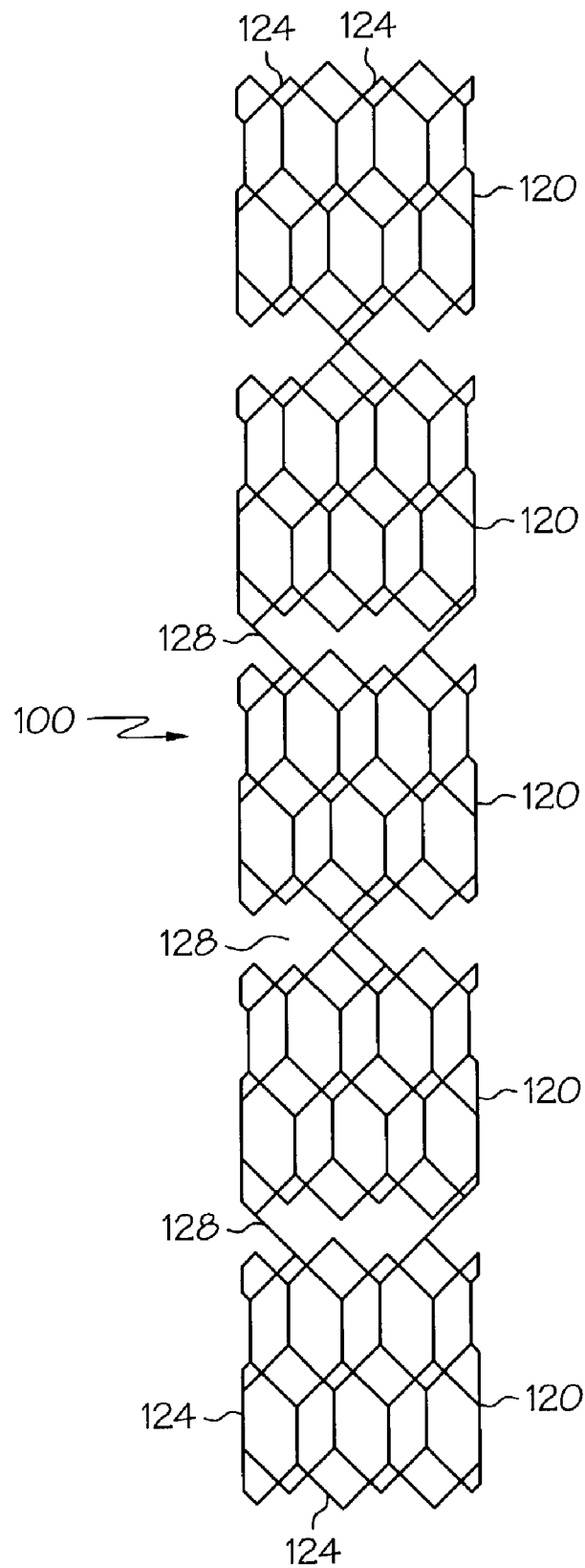
FIGS. 5a and 5b are views of embodiments of the invention in which connecting segments have been treated.
Figure 5B:
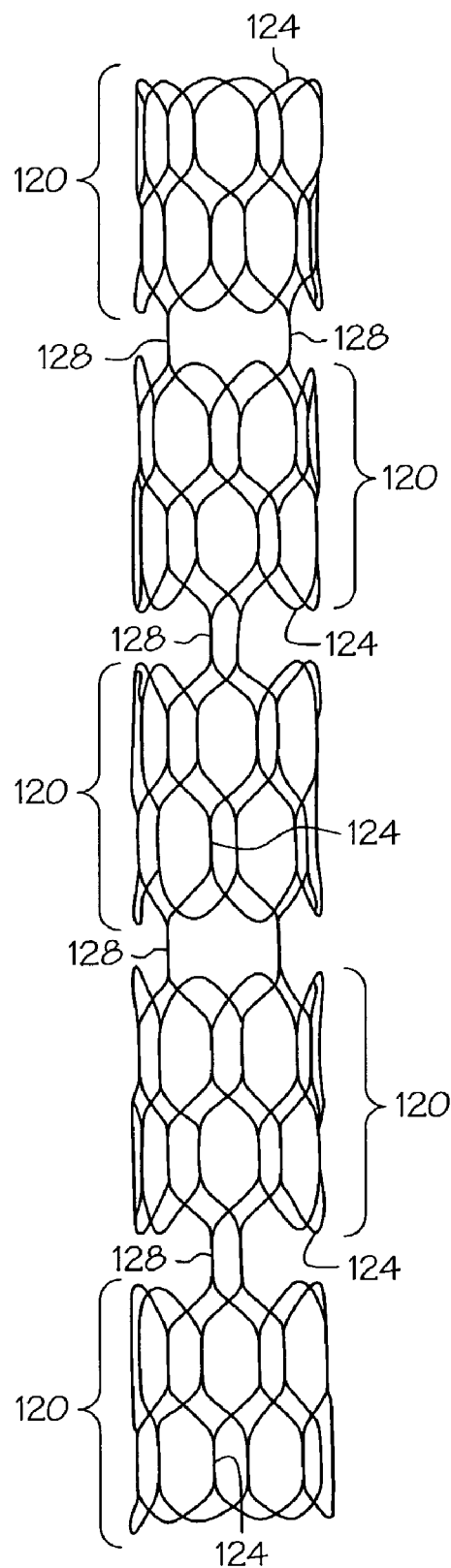

The invention is also directed to the stent shown generally at 100 in FIG. 5a, comprised of a plurality of spaced segments 120. Each segment 120 is desirably comprised of a series of interconnected cells 124. Desirably, cells 124 will be of polygonal configuration in plan view. More desirably, they will be hexagonal. Adjacent spaced segments 120 are connected to each other by one or more connector sections 128. Connector sections 128 may be disposed at an oblique angle relative to the longitudinal axis 180 of the stent as shown in FIG. 5a or they may be substantially parallel to the longitudinal axis 180 as shown in FIG. 5b. They may be straight or curved. Segments 120 have been subjected to a local heat treatment, in accordance with the invention. Desirably, segments 120 will be of lower stiffness than connector sections 128 as a result of the heat treatment.

Stent 100 may be made of any suitable shape-memory material including shape-memory metals such as Nitinol. Nitinol with a composition of about 55.75% (by weight) nickel and 44.25% (by weight) titanium may be particularly well suited for use in the present invention. The stent may be made of shape-memory wire or a sheet or tube of shape-memory material.

The invention is also directed to stents similar to those shown in FIGS. 5a and 5b, such as those disclosed in U.S. Ser. No. 08/942,162 incorporated herein in its entirety by reference, wherein the connector sections and the segments are subject to different heat treatments.

The stent configurations of FIGS. 3–5 are intended to be exemplary. Stents with other designs may be treated similarly.

Figure 6A:
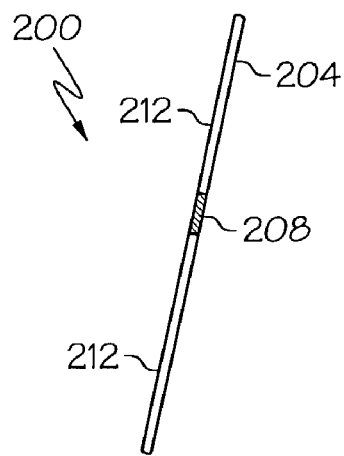
FIG. 6a shows a side elevational view of an inventive guidewire.

In another embodiment, the invention is directed to medical guidewires made of shape-memory materials, portions of which have been differentially treated. In one aspect of the invention, a medical guidewire, such as that shown at 200 in FIG. 6a, is specially treated toward distal end 204 of the guidewire. Region 208 of the device is heat treated to increase the tendency toward plastic deformation of the treated portion relative to the remainder of the guidewire. This, in turn, allows the guidewire to have a region of greater flexibility and a region of reduced flexibility corresponding to the locally treated section of the guidewire.

Figure 6B:
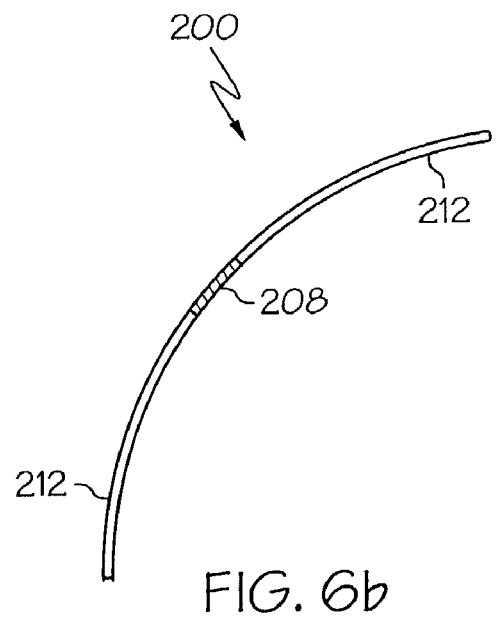
FIG. 6b shows the guidewire of FIG. 6a in a bent configuration.
Figure 6C:
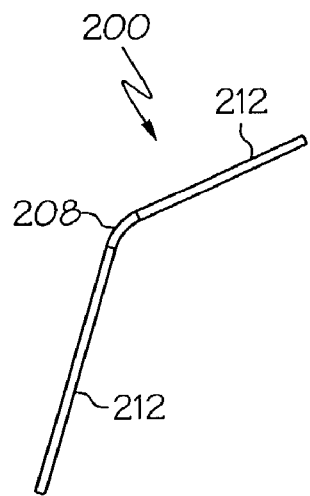
FIG. 6c shows the guidewire of FIG. 6b after it has been released from the bent configuration.

FIG. 6b and FIG. 6c illustrate the guidewire of FIG. 6a as it is bent and released. In FIG. 6b, guidewire 200 is bent. Region 208 has a greater tendency toward plastic deformation. The remainder 212 of guidewire 200 is in the austenitic state and thus deforms elastically. The guidewire of FIG. 6b is shown in FIG. 6c after it has been released from its bent position. Locally treated region 208 remains bent while austenitic regions 212 recovery fully to their configuration prior to being bent. Thus, by using Nitinol which has been treated to have spatially varying properties, it is possible to prepare a guidewire which may be permanently deformed within the body.

Figure 6D:
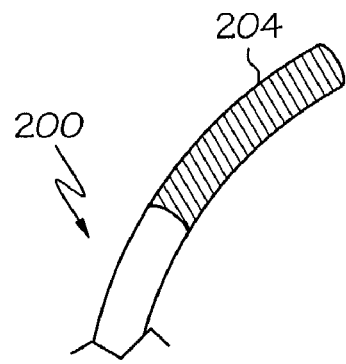
FIG. 6d shows a side elevational view of an inventive guidewire whose distal tip has been treated to exhibit a reduced stiffness.

A local heat treatment may also be used to reduce the stiffness of the tip of the guidewire prior to inserting the guidewire into the body. This is illustrated schematically in FIG. 6d. Distal end 204 of guidewire 200 has been subject to an additional heat treatment to reduce the stiffness of the distal end relative to the remainder of the guidewire. If the superelasticity is completely destroyed, a permanent bend may be placed in the guidewire, thereby allowing a physician to shape a guide wire as desired.

Figure 7A:
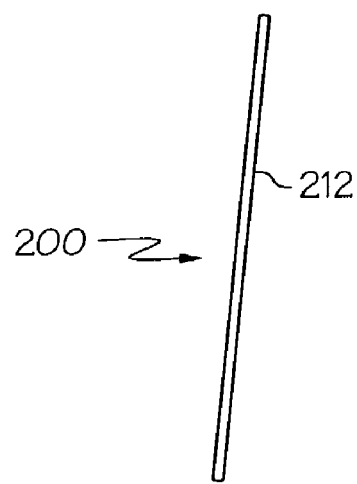
FIG. 7a shows a side elevational view of a prior art guidewire.
Figure 7B:
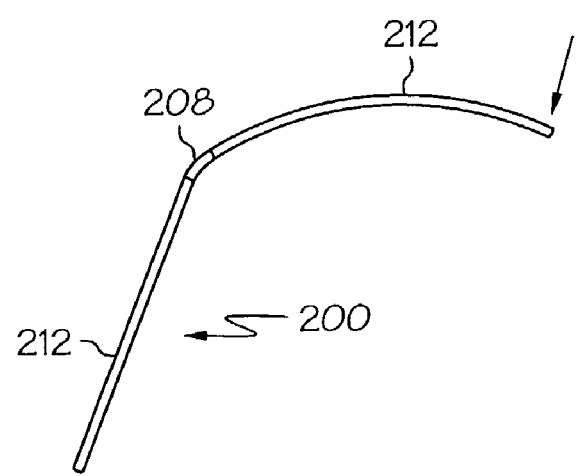
FIG. 7b shows the guidewire of FIG. 7a in a bent configuration.
Figure 7C:
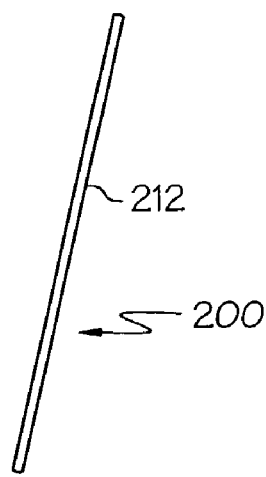
FIG. 7c shows the guidewire of FIG. 7b after it has been released from the bent configuration.

For the sake of comparison, a fully austenitic guidewire is shown in various states in FIGS. 7a–c. FIG. 7a shows guidewire 200. The entire guidewire is in the austenitic state 212. In. FIG. 7b, guidewire 200 is shown in a bent configuration. A small region 208 is in a stress-induced martensitic state while the remainder 212 of guidewire 200 is in the austenitic phase. Upon release of the guidewire, as shown in FIG. 7c, the entire guidewire returns to the configuration it had prior to being bent. The entire guidewire is in the austenitic state.

Figure 8:
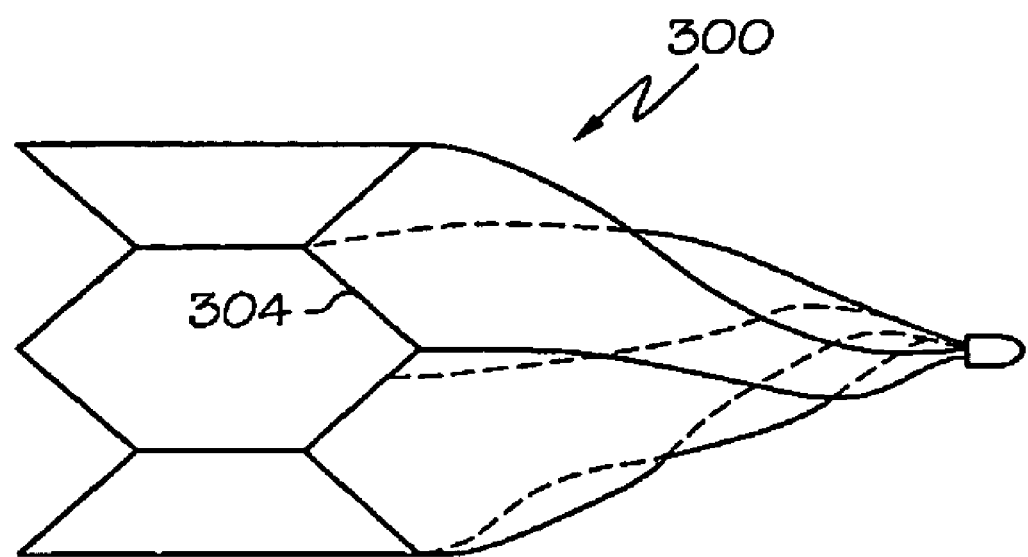
FIG. 8 shows a side elevational view of an inventive vena cava filter.

In yet another embodiment, the invention is directed to medical filters made, at least in part, of differentially treated shape-memory materials. FIG. 8 shows a vena cava filter generally at 300. Vena cava filter 300 is similar in design to that disclosed in commonly assigned U.S. Pat. No. 5,709,704 to Nott et al., the content of which is incorporated herein in its entirety by reference. Filter 300 is constructed, at least in part, of a shape memory material. Filter 300 includes a single cell 304 in which the shape-memory material is differentially heat treated to increase the tendency to plastic deformation of the desired portion of the filter. Although the filter of FIG. 8 shows an embodiment in which only a single cell has been heat treated differently, the invention contemplates other embodiment in which a plurality of cells has been differently treated. One such variant involves a filter comprised of multiple columns of cells, one of the columns having been subjected to a different heat treatment.

The invention may be practiced generally with shape-memory materials. Desirably, binary shape-memory metals such as Nitinol or other alloys of Nickel and Titanium will be used. The invention also contemplates the use of doped binary metals as well. Suitable dopants include Chromium, Niobium and Vanadium. Additional suitable shape-memory alloys are disclosed in WO 95/31945, the contents of which are incorporated herein in their entirety by reference.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method for making an expandable endoluminal device comprising at least one superelastic section and at least one plastically deformable section, the superelastic section and plastically deformable section comprising a continuous metallic structure in which the superelastic section has been thermally treated differently than the plastically deformable section, the method comprising: selecting a metallic member to be used for constructing the expandable endoluminal device; heat treating at least a first portion of the metallic member in a first annealing step under a first set of conditions to set a shape memory for at least the first portion; heat treating one or more second portions of the metallic member in a second annealing step under a second set of conditions to make the second portions plastically deformable; and forming the metallic member into the expandable endoluminal device such that the first portion comprises the superelastic section and the second portion comprises the plastically deformable section.

2. A method in accordance with claim 1 wherein the metallic member is a hollow tube, said heat treating one or more second portions comprises cutting the tube in a pattern to form the endoluminal device.

3. A method in accordance with claim 1 wherein the endoluminal device comprises a stent.

4. A method in accordance with claim 1 wherein the metallic member comprises a shape-memory material.

5. A method in accordance with claim 1 wherein the metallic member comprises a binary metallic material.

6. A method in accordance with claim 1 wherein the metallic material comprises nickel and titanium.

7. A method in accordance with claim 1 wherein the metallic material is doped with at least one of chromium, niobium, and vanadium.

8. A method in accordance with claim 1 wherein the first portion comprises the entire metallic member.

9. A method in accordance with claim 1 wherein the first set of conditions comprises an annealing temperature ranging from about 400 C. to about 575 C. and an annealing time of about zero to about 40 minutes.

10. A method in accordance with claim 9 wherein the annealing temperature ranges from about 450 C. to about 550 C.

11. A method in accordance with claim 9 wherein the annealing time ranges from about 10 minutes to about 15 minutes.

12. A method in accordance with claim 1 wherein the one or more second portions comprises one or more vertical stripes, one or more horizontal stripes, one or more isolated areas, or a combination thereof.

13. A method in accordance with claim 1 wherein the second annealing step comprises a localized heat treatment step performed by at least one of electrical resistance heating, inert gas jet heating, induction coil heating, laser heating, brazing, and fluidized bath heating with the second portion insulated.

14. A method in accordance with claim 1 wherein the second set of conditions comprises an annealing temperature ranging from about 550 C. to about 700 C. for a time period of about 5 minutes to about 20 minutes.

15. A method in accordance with claim 1 wherein the second set of conditions comprises an annealing temperature greater than about 650 C.

16. A method in accordance with claim 1 wherein the second set of conditions comprises an annealing temperature of about 550 C. to about 600 C. and an annealing time of about 5 minutes to about 20 minutes.

17. A method in accordance with claim 1 wherein forming the metallic member into the endoluminal device comprises a laser cutting technique or chemical etching.

18. A method in accordance with claim 1 further comprising attaching a graft as an inner liner or outer covering of the device.

19. A method for making an endoluminal device comprising at least one superelastic section and at least one plastically deformable section, the superelastic section and plastically deformable section comprising a continuous metallic structure in which the superelastic section has been thermally treated differently than the plastically deformable section, the method comprising: selecting a metallic member to be used for constructing the endoluminal device; heat treating at least a first portion of the metallic member in a first annealing step under a first set of conditions to set a shape memory for at least the first portion; heat treating one or more second portions of the metallic member in a second annealing step under a second set of conditions to make the second portions plastically deformable; and forming the metallic member into the endoluminal device such that the first portion comprises the superelastic section and the second portion comprises the plastically deformable section; wherein the metallic material is doped with at least one of chromium, niobium, and vanadium.

20. A method for making an endoluminal device comprising at least one superelastic section and at least one plastically deformable section, the superelastic section and plastically deformable section comprising a continuous metallic structure in which the superelastic section has been thermally treated differently than the plastically deformable section, the method comprising: selecting a metallic member to be used for constructing the endoluminal device; heat treating at least a first portion of the metallic member in a first annealing step under a first set of conditions to set a shape memory for at least the first portion; heat treating one or more second portions of the metallic member in a second annealing step under a second set of conditions to make the second portions plastically deformable; and forming the metallic member into the endoluminal device such that the first portion comprises the superelastic section and the second portion comprises the plastically deformable section; wherein the first portion comprises the entire metallic member.

21. A method for making an endoluminal device comprising at least one superelastic section and at least one plastically deformable section, the superelastic section and plastically deformable section comprising a continuous metallic structure in which the superelastic section has been thermally treated differently than the plastically deformable section, the method comprising: selecting a metallic member to be used for constructing the endoluminal device; heat treating at least a first portion of the metallic member in a first annealing step under a first set of conditions to set a shape memory for at least the first portion; heat treating one or more second portions of the metallic member in a second annealing step under a second set of conditions to make the second portions plastically deformable; and forming the metallic member into the endoluminal device such that the first portion comprises the superelastic section and the second portion comprises the plastically deformable section; wherein the second annealing step comprises a localized heat treatment step performed by at least one of electrical resistance heating, inert gas jet heating, induction coil heating, laser heating, brazing, and fluidized bath heating with the second portion insulated.

22. A method for making an endoluminal device comprising at least one superelastic section and at least one plastically deformable section, the superelastic section and plastically deformable section comprising a continuous metallic structure in which the superelastic section has been thermally treated differently than the plastically deformable section, the method comprising: selecting a metallic member to be used for constructing the endoluminal device; heat treating at least a first portion of the metallic member in a first annealing step under a first set of conditions to set a shape memory for at least the first portion; heat treating one or more second portions of the metallic member in a second annealing step under a second set of conditions to make the second portions plastically deformable; and forming the metallic member into the endoluminal device such that the first portion comprises the superelastic section and the second portion comprises the plastically deformable section; further comprising attaching a graft as an inner liner or outer covering of the device.

* * * * *